United States Patent
Eisele et al.

(10) Patent No.: US 10,238,802 B2
(45) Date of Patent: Mar. 26, 2019

(54) SYRINGE WITH A FIRST AND A SECOND SYRINGE BARREL

(71) Applicant: Henke-Sass, Wolf GmbH, Tuttlingen (DE)

(72) Inventors: Melanie Eisele, Wurmlingen (DE); Frank Altermann, Tuttlingen (DE)

(73) Assignee: Henke-Sass, Wolf GmbH, Tuttlingen (DE)

(*) Notice: Subject to any disclaimer, the term of this patent is extended or adjusted under 35 U.S.C. 154(b) by 422 days.

(21) Appl. No.: 15/063,490

(22) Filed: Mar. 7, 2016

(65) Prior Publication Data

US 2016/0263321 A1   Sep. 15, 2016

(30) Foreign Application Priority Data

Mar. 13, 2015   (DE) .................... 10 2015 103 750

(51) Int. Cl.
| | |
|---|---|
| *A61D 1/00* | (2006.01) |
| *A61M 5/19* | (2006.01) |
| *A61M 5/20* | (2006.01) |
| *A61M 5/32* | (2006.01) |
| *A61M 5/34* | (2006.01) |
| *A61M 5/315* | (2006.01) |

(52) U.S. Cl.
CPC ............... *A61M 5/19* (2013.01); *A61D 1/00* (2013.01); *A61M 5/3298* (2013.01); *A61M 5/204* (2013.01); *A61M 5/31581* (2013.01); *A61M 2005/342* (2013.01); *A61M 2250/00* (2013.01)

(58) Field of Classification Search
CPC .. A61M 5/2066; A61M 5/2448; A61M 5/284; A61M 5/3294; A61M 5/3295; A61M 5/3298; A61M 5/31581; A61M 5/19; A61M 5/007; A61M 5/342; A61D 7/00; A61D 1/025
See application file for complete search history.

(56) References Cited

U.S. PATENT DOCUMENTS

| | | | |
|---|---|---|---|
| 1,367,008 A | * | 2/1921 | Bessese ............... A61M 5/204 604/184 |
| 4,609,371 A | | 9/1986 | Pizzino |
| 4,610,666 A | | 9/1986 | Pizzino |

(Continued)

FOREIGN PATENT DOCUMENTS

| | | |
|---|---|---|
| DE | 102011081797 A1 | 2/2013 |
| WO | 03075978 A2 | 9/2003 |
| WO | 2012013587 A1 | 2/2012 |

*Primary Examiner* — Nathan R Price
*Assistant Examiner* — Dung T Ulsh
(74) *Attorney, Agent, or Firm* — Skaar Ulbrich Macari, P.A.

(57) ABSTRACT

A syringe includes a first syringe barrel and a second syringe barrel. Each barrel includes a delivery end to which an end piece with a channel is secured, a piston which is arranged movable in the syringe barrel and can be moved towards the delivery end in order to deliver a fluid located between the delivery end and the piston via the channel. The two syringe barrels are mechanically connected to each other such that the distance between them cannot be changed. At least one of the two end pieces can be secured to the allocated delivery end in different positions for adjustment of the distance between the two channels.

20 Claims, 3 Drawing Sheets

(56) References Cited

U.S. PATENT DOCUMENTS

| | | | |
|---|---|---|---|
| 2006/0229563 A1* | 10/2006 | O'Reagan | A61M 25/0631 604/164.08 |
| 2009/0127289 A1 | 5/2009 | Keller | |
| 2009/0306621 A1 | 12/2009 | Thome, Jr. et al. | |
| 2011/0106054 A1* | 5/2011 | Osborne | A61B 17/8816 604/518 |

* cited by examiner

SYRINGE WITH A FIRST AND A SECOND SYRINGE BARREL

PRIORITY

This application claims the benefit of German Patent Application No. 102015103750.5, filed on Mar. 13, 2015, which is hereby incorporated herein by reference in its entirety.

FIELD

The present invention relates to a syringe with a first and a second syringe barrel.

BACKGROUND

Double-barrelled syringes are often used e.g. in the veterinary field in order to administer two different medicines to the animals at the same time. In order that the syringe has a field of use that is as large as possible, and thus can be used for a wide variety of animals, it is helpful if the distance between the hollow-bore needles which can be connected to the syringe barrels is settable. For this, in the simplest case, the distance between the syringe barrels, and thus also the distance between the needles, can be provided alterable. However, as a rule, this leads to an expensive mechanism and to difficulties with the stability of the syringe.

SUMMARY

An object of the invention is to provide a syringe with two syringe barrels, in which it is easily possible to adjust the distance between the delivery ends.

The disclosure includes a syringe with a first syringe barrel which comprises a first delivery end to which a first end piece with a first channel is secured, a first piston which is arranged movable in the first syringe barrel and can be moved towards the first delivery end in order to deliver a fluid located between the first delivery end and the first piston via the first channel, a second syringe barrel which comprises a second delivery end to which a second end piece with a second channel is secured, and a second piston which is arranged movable in the second syringe barrel and can be moved towards the second delivery end in order to deliver a fluid located between the second delivery end and the second piston via the second channel, wherein the two syringe barrels are mechanically connected to each other such that the distance between them cannot be changed, and wherein at least one of the two end pieces can be secured to the allocated delivery end in different positions for the adjustment of the distance between the two channels.

Only the at least one of the two end pieces has to be secured to the associated delivery end in different positions for the adjustment of the distance between the channels, the desired distance can be easily set. At the same time the stability of the syringe is not impaired, as the distance between the syringe barrels themselves cannot be changed, and thus the mechanical connection between the syringe barrels can be dimensioned such that the required stability is securely provided.

The disclosure includes a syringe, which can be formed as a veterinary syringe, wherein the at least one of the two end pieces can be secured to the allocated delivery end in different rotational positions about a centre axis of the end piece, wherein the channel of the at least one of the two end pieces is arranged eccentrically relative to the centre axis of the end piece. After the rotation of the end piece about the centre axis has taken place, the eccentric arrangement of the channel leads to a change in the distance between the channels depending on the rotational position of the end piece.

The at least one of the two end pieces can comprise an end which faces the allocated syringe barrel and can be inserted in at least two different rotational positions into a receiver provided at the delivery end of the allocated syringe barrel. In particular, it can be fixed or locked in the different rotational positions, with the result that an undesired change in the rotational position is securely prevented. A fixing device can be provided for the fixing or locking.

The receiver can in particular be formed in the shape of a hollow cylinder and the corresponding end can be formed cylindrical. In particular, the hollow cylinder-shaped recess can have an n-sided contour (or a contour with n sides) and the corresponding end can have an m-sided contour (or a contour with m sides), wherein n and m are whole numbers and n is greater than or equal to m. It is thus possible to predefine n different rotational positions in which the end piece can be secured. In cross section the n- and m-sided contour preferably have the shape of an (in particular regular) polygon with n or, respectively, m corners.

In certain embodiments, the at least one of the two end pieces can be secured to the allocated delivery end by means of a union nut. The desired fixing is thus easily provided. The two end pieces can be formed such that a hollow-bore needle can be detachably secured to them in each case. The two syringe barrels can be aligned parallel to each other. In addition, the two channels can be aligned parallel to each other. The syringe also can be configured as a self-filling syringe.

The disclosure also includes a syringe comprising a main part to which the two syringe barrels are mechanically secured. A lever with which the pistons can be moved back and forth in the two syringe barrels (for example via piston rods) can be hinged to the main part. In particular, the lever can be hinged to an end of the main part facing away from the syringe barrels. The lever and the main part can be pre-tensioned by a spring. The syringe can in particular be formed like a gun, with the result that a user can grip the main part with four fingers and the lever with his thumb and, by closing his hand, can then move the lever in the direction of the delivery ends in order to carry out the desired syringing.

A feed channel can be provided in at least one of the two pistons, wherein the feed channel opens into the first or second syringe barrel. The respective syringe barrel can be filled with the fluid to be delivered via the feed channel.

The first piston can be connected to a first piston rod which extends beyond a rear end of the first syringe barrel facing away from the first delivery end, the second piston can be connected to a second piston rod which extends beyond the rear end of the second syringe barrel facing away from the second delivery end, wherein the feed channel of the at least one of the two pistons (or of both pistons) extends through the piston rod connected thereto. The fluid to be delivered can be filled in the syringe barrel via the feed channel.

Further, the feed channel extending through the piston rod can open into a connection at the end facing away from the piston to which the piston rod is connected, wherein a first non-return valve is provided within the connection and opens when the piston is moved away from the delivery end. The connection is preferably connected with a reservoir of the fluid to be delivered.

The disclosure includes a syringe comprising a second non-return valve in at least one of the two delivery ends, wherein the second non-return valve opens when the respective piston is moved towards the delivery end.

The syringe can be formed partially or completely from plastic.

The syringe barrels and/or the end pieces can be formed identically. However, it is also possible for them to differ. For example, the diameters of the syringe barrels can be different.

In addition, the syringe according to the invention can be configured as an injection needle or hollow-bore needle at each delivery end.

The first channel can be in fluid connection to the first syringe barrel and the second channel can be in fluid connection to the second syringe barrel. In particular, an adapter is provided in each case between the first/second channel and the first/second syringe barrel.

It is understood that the features mentioned above and those yet to be explained below can be used not only in the stated combinations but also in other combinations or alone, without departing from the scope of the present invention.

Figure 1:
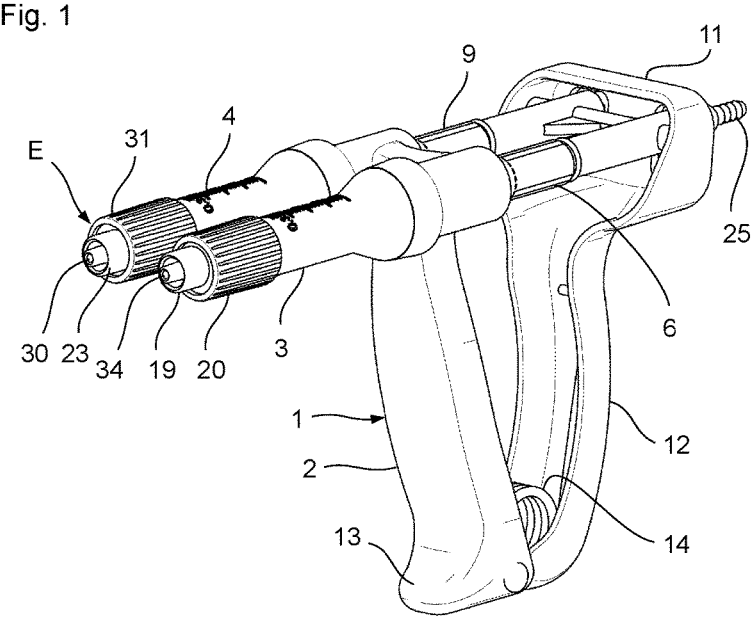
FIG. 1 is a perspective view of an embodiment of the syringe according to the invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various exemplary embodiments. Nevertheless, these embodiments are not intended to limit the present invention to any specific example, environment, application, or particular implementation described herein. Therefore, descriptions of these example embodiments are only provided for purpose of illustration rather than to limit the present invention.

Figure 2:
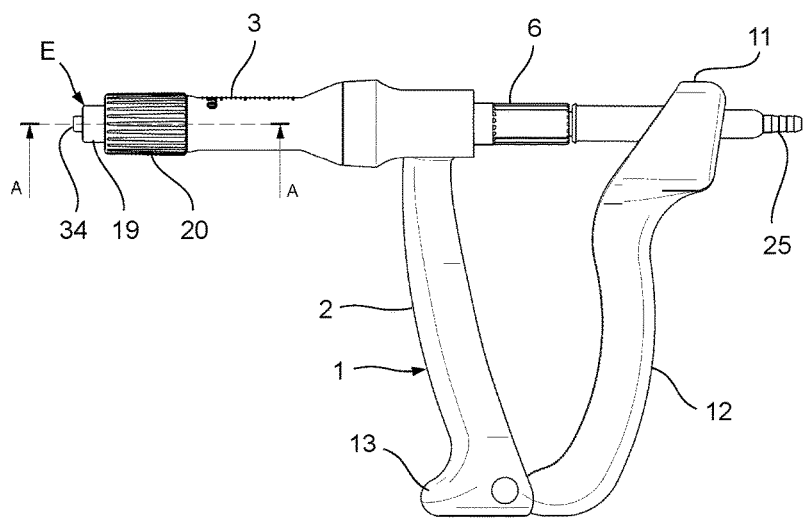
FIG. 2 is a side view of the syringe from FIG. 1.

In the embodiment shown in FIGS. 1 and 2 the syringe 1 according to the invention comprises a main part 2, on which a first and a second syringe barrel 3, 4 are formed. As can be seen in particular from the sectional view in FIG. 3, a first piston 5 which can be moved back and forth in the first syringe barrel 3 or in the first syringe cavity 7 provided by the first syringe barrel 3 via a first piston rod 6 connected to the first piston 5 is arranged in the first syringe barrel 3. The second syringe barrel 4 is formed in the same way as the first syringe barrel 3 and comprises a second piston 8 which can be moved back and forth in the second syringe cavity 10 provided by the second syringe barrel 4 via a second piston rod 9 which is connected to the second piston 8.

The two piston rods 6, 9 are guided out via the rear ends (not shown) of the syringe cavities 7, 10 and connected to an upper end 11 of a lever 12 swivellably connected to the main part 2 (FIGS. 1, 2). The lever 12 is swivellably connected to the main part 2 at the lower end 13 pointing away from the syringe barrels 3, 4, wherein a spring 14 arranged in the area of the lower end 13 pushes the main part 2 and the lever 12 apart, with the result that the starting position shown in FIGS. 1 and 2 exists. If the lever 12 is moved towards the main part 2 against the force of the spring 14, the two piston rods 6 and 9, and thus the two pistons 5 and 8, are thereby moved to the syringing-side end E of the syringe 1. In the sectional representation from FIG. 3 this leads to a movement of the pistons 5, 9 towards the left.

Figure 3:
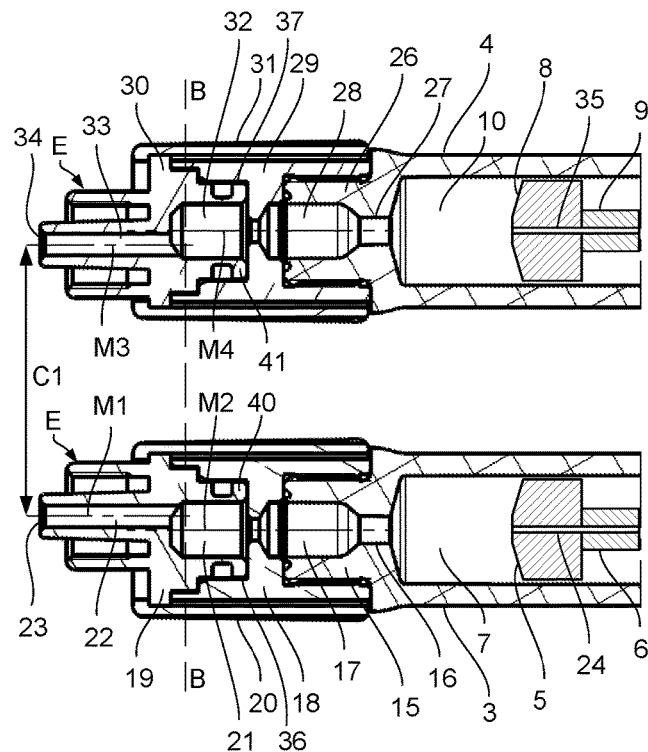
FIG. 3 is an enlarged sectional view along the section line A-A from FIG. 2.

As can be seen in particular from the sectional representation in FIG. 3, at its delivery end 15 the first syringe barrel 3 comprises a first connecting channel 16, which connects the first syringe cavity 7 to a first valve chamber 17. At the delivery end 15 a first adapter 18 is mounted (for example screwed on), in which a first end piece 19 sits which, for its part, is secured to the first adapter 18 by means of a first union nut 20. The first end piece 19 comprises a first interspace 21 which is connected to the first valve chamber 17 via the first adapter 18. The first interspace 21 opens into a first channel 22 in the first end piece 19 and the first channel 22 comprises a first delivery opening 23. A fluid which is present in the first syringe cavity 7 between the first piston 5 and the first delivery end 15 can thus be delivered to the outside by movement of the first piston 5 towards the first delivery end 15 via the first connecting channel 16, the first valve chamber 17, the first adapter 18, the first interspace 21 and the first channel 22. As can be seen from the sectional representation in FIG. 3, the first syringe cavity 7, the first connecting channel 16, the first valve chamber 17 and the first interspace 21 are arranged coaxially relative to each other. The first channel 22, on the other hand, is arranged not coaxially relative to the first interspace 21 and the first syringe cavity 7 but offset relative to the corresponding centre axis M1 of the first end piece 19. The centre axis M1 of the first channel 22 is preferably, as shown in FIG. 3, parallel to the centre axis M2 of the first end piece 19. Furthermore, the centre axis M1 of the first channel 22 can be parallel to the centre axis of the first syringe cavity 7 or of the first interspace 21.

The syringe 1 is formed as a self-filling syringe and, for this, in the first valve chamber 17, comprises a non-return valve, not represented, which seals the first connecting channel 16 during a movement of the first piston 5 from left to right (thus away from the first delivery end 15) and opens it during a contrary movement of the first piston 5 (thus towards the first delivery end 15). In the first piston 5 and the first piston rod 6 a first feed channel 24 is formed which extends up to a first connection 25 arranged at the rear end of the syringe 1, wherein in the first connection 25 in turn a non-return valve, not shown, is arranged which opens during a movement of the first piston 5 away from the first delivery end 15, and thus towards the first connection 25, and closes during the contrary movement. A fluid reservoir (e.g. a medicine to be injected) is attached to the first connection 25 during use of the syringe 1, with the result that the first syringe cavity 7 is filled with fluid during a movement of the first piston 5 away from the first delivery end 15 and the fluid is delivered or syringed out of the first delivery opening 23 during a contrary movement of the first piston 5 (thus towards the first delivery end 15).

As is shown in FIG. 3, the second piston 8 is formed identical in construction to the first piston and comprises a second delivery end 26, a second connecting channel 27, a second valve chamber 28, a second adapter 29, a second end piece 30, a second union nut 31, a second interspace 32, a second channel 33, a second delivery opening 34 and a second feed channel 35. A second connection is also provided which, however, is not visible in the figures. Furthermore, the centre axis M3 of the second end piece 30, in the same way as with the first end piece 19, is eccentric relative to the centre axis M4 of the second channel 33.

The two syringe barrels 3, 4 are mechanically connected to the main part 2 such that the distance between them cannot be altered. However, the two end pieces 19, 30, as described in detail in the following, can be set into different rotational positions in the respective adapter 18, 29, with the result that the distance between the two delivery openings 23, 34 is variable.

Figure 4:
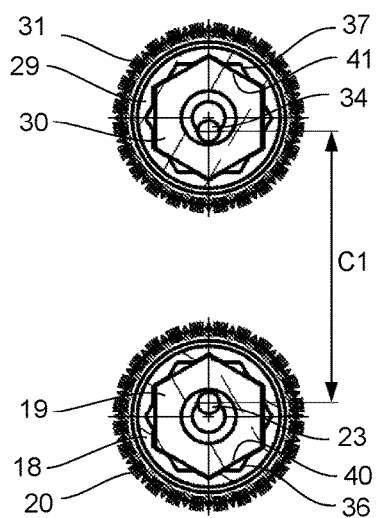
FIG. 4 is a sectional view along the section line B-B from FIG. 3.
Figure 5:
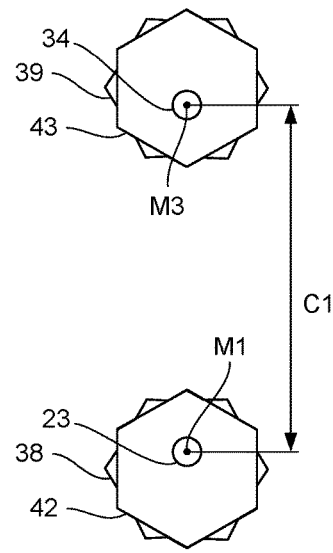
FIGS. 5 to 8 are schematic representations to explain different rotational positions of the end pieces relative to the syringe barrel.

For this, the respective adapter 18, 29 comprises a receiver 36, 37 with a double-hexagon contour 38, 39. The end 40, 41 of the respective end piece 19, 30 inserted into the respective receiver 36, 37 in each case has a hexagonal outer contour 42, 43, with the result that each end piece 19, 30 can be inserted into the allocated receiver 36, 37 in twelve different rotational positions and locked by means of the union nuts 20, 31. Once the channels 22, 33 have been arranged, not coaxially but eccentrically, in the respective end piece 18, 30, the distance between the two channels 22 and 33, and thus between the two delivery openings 23 and 34, can be set by the choice of the rotational positions of the two end pieces 19, 30. In the representations from FIGS. 3 and 4 the minimum distance C1 is shown, which is 25 mm here. For clarification, in FIG. 5 the same state of the two end pieces 19 and 30 as in FIGS. 3 and 4 is shown, wherein in the representation from FIG. 5 only the two contours 38, 39, as well as 41 and 42, the two delivery openings 23 and 34 and the corresponding centre axis of the two channels 22 and 33 are represented.

Figure 6:
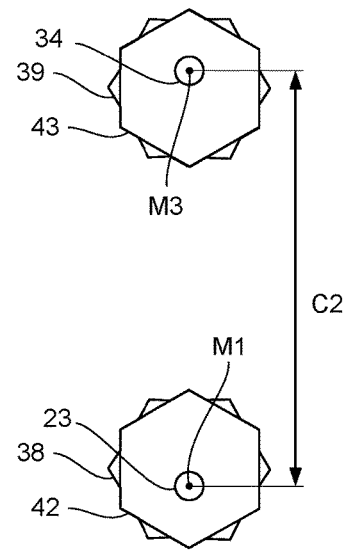

In the rotational position of the two end pieces 19, 30 shown in FIG. 6, the maximum settable distance C2 between the two delivery openings 23 and 34 (or between their centre axes M1 and M3) exists, which is 30 mm here.

Figure 7:
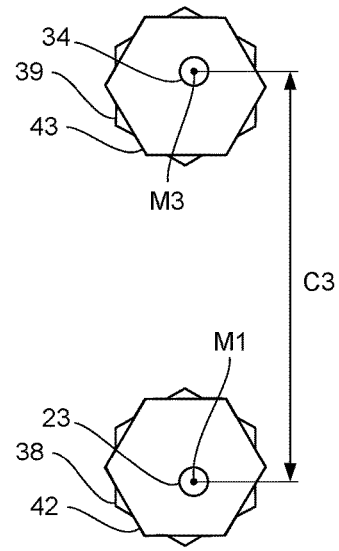

In the case of the choice of the rotational positions of the two end pieces 19, 30 shown in FIG. 7, a distance C3 between the two delivery openings 23 and 34 which lies between the two distances C1 and C2 exists.

Figure 8:
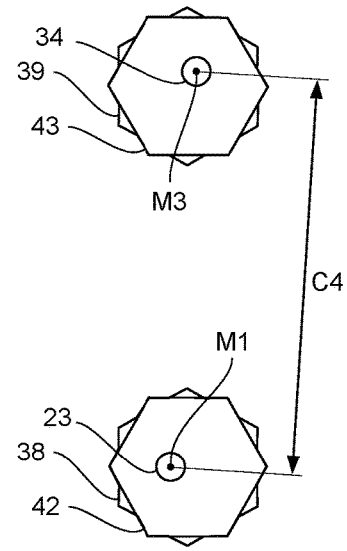

In FIG. 8 rotational positions of the end pieces 19, 30 are shown in which the rotational position is not mirror-symmetrical to a centre plane which lies between the two syringe barrels 3 and 4 and extends from the upper end 11 to the lower end 13 (a plane parallel to the plane of drawing according to FIG. 2).

The distance between the delivery openings 23 and 34 can thus be altered and set as required by the formation according to the invention of the syringe 1 and in particular of the end pieces 19 and 30 in connection with the adapters 18 and 29.

The end pieces 19 and 30 are in particular formed such that injection needles (not shown) can be provided. At the same time the distance between the injection needles is then also changed and set by adjustment of the distance between the two delivery openings 23 and 34.

In the described embodiment the syringe 1 according to the invention is formed as a self-filling syringe. This need not be the case. It can also be formed as a syringe 1 which is not a self-filling syringe.

In the embodiment described the two syringe barrels 3 and 4 are formed identical in construction. This is not strictly necessary. For example the inside diameter of the first syringe barrel 3 can be different from the inside diameter of the second syringe barrel 4. The syringe barrels 3 and 4 can comprise syringe cavities 7 and 10 with a volume of e.g. 1.0-5.0 ml.

Furthermore, it is also possible to provide more than two syringe barrels 3, 4 if this is desired.

The syringe according to the invention is in particular formed such that the maximum piston stroke, and thus the dosage per syringing procedure, can be set for each of the two pistons 5 and 8 independently of each other. The piston stroke can thus be the same or different for both pistons 5, 8.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. A syringe, comprising:
   a first syringe barrel which includes a first delivery end to which a first end piece with a first channel is secured, the first channel defining a centre axis of the first channel;
   a first piston which is arranged movable in the first syringe barrel and is configured to be moved towards the first delivery end in order to deliver a fluid located between the first delivery end and the first piston via the first channel;
   a second syringe barrel which includes a second delivery end to which a second end piece with a second channel is secured, the second channel defining a centre axis of the second channel; and
   a second piston which is arranged movable in the second syringe barrel and which is configured to be moved towards the second delivery end in order to deliver a fluid located between the second delivery end and the second piston via the second channel,
   wherein the first syringe barrel and the second syringe barrel are mechanically connected to each other such that a distance between them cannot be changed, and
   wherein at least one of the first end piece and second end piece is configured to be secured to an allocated delivery end in different rotational positions for the adjustment of a perpendicular distance defined between the centre axis of the first channel and the centre axis of the second channel.

2. The syringe according to claim 1, wherein the at least one of the first end piece and second end piece is configured to be secured to the allocated delivery end in multiple different axial rotational positions that are each arranged eccentrically relative to a respective centre axis of the the first end piece and second end piece.

3. The syringe according to claim 1, wherein the at least one of the first end piece and second end piece comprises an end which faces the corresponding syringe barrel and which is insertable in at least two different rotational positions into a receiver provided at a corresponding delivery end of the corresponding syringe barrel.

4. The syringe according to claim 3, further comprising a fixing device provided to at least one of the first end piece and second end piece to fix the at least one of the first end piece and second end piece in a chosen rotational position.

5. The syringe according to claim 4, wherein the receiver is shaped as a hollow cylinder and the corresponding delivery end is cylindrical.

6. The syringe according to claim 5, wherein the hollow cylinder-shaped receiver defines a contour with n sides and the at least one of the first end piece and second end piece defines a contour with m sides, wherein n and m are whole numbers and n is greater than or equal to m.

7. The syringe according to claim 4, further comprising:
a main part, to which the first syringe barrel and the second syringe barrel are secured; and
a lever which is hinged to the main part and which is connected to the first piston and the second piston in order to move them towards the respective first delivery end and second delivery end when the lever is actuated.

8. The syringe according to claim 4, wherein a feed channel, which opens to one of the first syringe barrel and the second syringe barrel, is formed in at least one of the first piston and the second piston.

9. The syringe according to claim 4,
wherein the first piston is connected with a first piston rod, which extends beyond a rear end of the first syringe barrel facing away from the first delivery end,
wherein the second piston is connected to a second piston rod, which extends beyond a rear end of the second syringe barrel facing away from a second delivery end, and
wherein a feed channel of the at least one of the first piston and the second piston extends through the respective first piston rod or second piston rod connected with said at least one of the first piston and the second piston.

10. The syringe according to claim 3, wherein the receiver is shaped as a hollow cylinder and the corresponding delivery end is cylindrical.

11. The syringe according to claim 10, wherein the hollow cylinder-shaped receiver defines a contour with n sides and the at least one of the first end piece and second end piece defines a contour with m sides, wherein n and m are whole numbers and n is greater than or equal to m.

12. The syringe according to claim 1, wherein the at least one of the first end piece and the second end piece is secured to the corresponding delivery end by a union nut.

13. The syringe according to claim 1, wherein each of the first end piece and the second end piece are configured such that a hollow-bore needle is configured to be detachably secured thereto.

14. The syringe according to claim 1, wherein the first syringe barrel and the second syringe barrel are each aligned parallel to one another and wherein the first channel and the second channel are each aligned parallel to one another.

15. The syringe according to claim 1, wherein the syringe is configured as a self-filling syringe.

16. The syringe according to claim 1, further comprising:
a main part, to which the first syringe barrel and the second syringe barrel are secured; and
a lever which is hinged to the main part and which is connected to the first piston and the second piston in order to move them towards the respective first delivery end and second delivery end when the lever is actuated.

17. The syringe according to claim 1, wherein a feed channel, which opens to one of the first syringe barrel and the second syringe barrel, is formed in at least one of the first piston and the second piston.

18. The Syringe according to claim 17,
wherein the first piston is connected with a first piston rod, which extends beyond a rear end of the first syringe barrel facing away from the first delivery end,
wherein the second piston is connected to a second piston rod, which extends beyond a rear end of the second syringe barrel facing away from a second delivery end, and
wherein the feed channel of the at least one of the first piston and the second piston extends through the respective first piston rod or second piston rod connected with said at least one of the first piston and the second piston.

19. The syringe according to claim 18,
wherein the feed channel, which extends through the respective first piston rod or second piston rod connected with said at least one of the first piston and the second piston, opens to a connection at the respective first delivery end and second delivery end facing away from the respective first piston rod or second piston rod connected with said at least one of the first piston and the second piston, and
wherein a non-return valve is provided in the connection and opens when the respective first piston rod or second piston rod connected with said at least one of the first piston and the second piston is moved away from the respective first delivery end and second delivery end.

20. The syringe according to claim 1, wherein a non-return valve is provided in at least one of the first delivery end and second delivery end and opens, when the corresponding first piston or second piston is moved towards the corresponding first delivery end and second delivery end.

* * * * *